(12) United States Patent
Tanaka et al.

(10) Patent No.: US 8,771,654 B2
(45) Date of Patent: Jul. 8, 2014

(54) ARTIFICIAL NAIL COMPOSITION HAVING EXCELLENT APPEARANCE

(75) Inventors: Hisaki Tanaka, Kyoto (JP); Mikito Deguchi, Kyoto (JP)

(73) Assignee: Kabushiki Kaisha Shofu, Kyoto (JP)

(*) Notice: Subject to any disclaimer, the term of this patent is extended or adjusted under 35 U.S.C. 154(b) by 129 days.

(21) Appl. No.: 12/457,244

(22) Filed: Jun. 4, 2009

(65) Prior Publication Data

US 2009/0304612 A1    Dec. 10, 2009

Related U.S. Application Data

(63) Continuation-in-part of application No. 12/314,971, filed on Dec. 19, 2008, now abandoned.

(30) Foreign Application Priority Data

Jun. 5, 2008  (JP) ................................. 2008-147720
May 20, 2009  (JP) ................................. 2009-121506

(51) Int. Cl.
| | |
|---|---|
| *A61K 8/00* | (2006.01) |
| *A61K 8/02* | (2006.01) |
| *A61K 8/18* | (2006.01) |
| *A61Q 3/02* | (2006.01) |

(52) U.S. Cl.
CPC .... *A61K 8/18* (2013.01); *A61Q 3/02* (2013.01)
USPC .......................................... 424/61; 424/401

(58) Field of Classification Search
None
See application file for complete search history.

(56) References Cited

U.S. PATENT DOCUMENTS 5,830,442 A * 11/1998 Beaver ............................ 424/61
2005/0257335 A1 * 11/2005 Dumousseaux ................ 8/406

FOREIGN PATENT DOCUMENTS

EP    1241959    * 12/2000
JP    2002-161025    6/2002

OTHER PUBLICATIONS

Linz et al., Color-Travel Cosmetic Pigments: Interference to the Max, Cosmetics & Toiletries, vol. 188, No. 12 (2003), pp. 63-70.*
SunChemical Performance Pigments, http://www.in-cosmeticsasia.com/ExhibitorLibrary/293/SunCROMA_1.pdf, accessed Dec. 29, 2011.*
Office Action in corresponding Japanese application JP 2009-121506 dated May 7, 2013.

* cited by examiner

*Primary Examiner* — Cherie M Stanfield
*Assistant Examiner* — Melissa Javier
(74) *Attorney, Agent, or Firm* — Wenderoth, Lind & Ponack, L.L.P.

(57) ABSTRACT

The present invention provides an artificial nail composition which can easily impart a special appearance to the tip of the finger, and which is an artificial nail material coated on a natural or artificial nail, and is used by coating on the surface of a natural or artificial nail followed by polymerization and, more particularly, an artificial nail composition which is vivid and has a natural color tone having a transparent sensation, that cannot be achieved by a conventionally used artificial nail composition containing an organic and/or inorganic colorant utilizing absorption and/or a scattering phenomenon of light, and imparts special appearance by an interference color.

2 Claims, 15 Drawing Sheets

ARTIFICIAL NAIL COMPOSITION HAVING EXCELLENT APPEARANCE

This is a CIP application of Ser. No. 12/314,971, filed Dec. 19, 2008 now abandoned.

BACKGROUND OF THE INVENTION

1. Field of the Invention

The present-invention relates to a composition which is an artificial nail material coated on a natural or artificial nail, and is used by coating on the surface of a natural or artificial nail followed by polymerization. More particularly, the present invention relates to an artificial nail composition containing a compound having at least one radical polymerizable unsaturated double bond in the molecule, a radical polymerization initiator, an organic and/or inorganic colorant utilizing an absorbing and/or scattering phenomenon of light, and an organic and/or inorganic colorant utilizing an interference phenomenon of light. A particularly beautiful appearance can be easily imparted to the tip of the finger by using the composition of the present invention.

2. Description of the Related Art

Nail art means makeup or decoration of nails of the hands and feet. A shop for nail art is called a nail salon and a technician in a nail art field is called a nail technician. Various nail art goods are commercially available and there are many women who perform nail art with skill equivalent to a professional.

An artificial nail material utilizing a dental resin which is polymerizable at room temperature has excellent strength and durability when compared with a manicure utilizing a lacquer composition and is therefore accepted by some professional nail technicians. However, due to irritation and irritating odor caused by an acryl monomer and poor operability, such an artificial nail material is not generally used by nail technicians.

Recently, a gel nail obtained by improving odor irritation and operability of a dental resin which is polymerizable at room temperature utilizing an artificial nail material is popular in the market. A gel nail which is now commercially available is a high-viscosity liquid material containing a (meth)acryl-based monomer and a photopolymerization initiator as main components and is cured by irradiation with ultraviolet rays. Commercially available gel nails cause less odor irritation or skin irritation, have excellent operability and also have various color tones when compared with the above-described dental resin which is polymerizable at room temperature. As a result, they are accepted by the majority of general nail technicians. However, the color tones of commercially available gel nails cannot meet aesthetic demands of consumers.

A gel nail product which is now commercially available is an artificial nail composition containing an organic and/or inorganic colorant utilizing an absorbing and/or scattering phenomenon of light that has been utilized for a long time. This gel nail product has a problem that the color and transparency deteriorate as a result of light absorption of a colorant. Basically, a metallic pigment obtained by total reflection of light is typically a metallic aluminum flake. A pigment utilizing regular multiple reflection and interference principle of light is typically a pearl pigment. Although gel nail products utilizing these pigments are commercially available, these products basically have a monotonous color tone which intends to obtain silky sensation and glittering sensation by silver luster, and thus these products did not meet the aesthetic demand of consumers.

Japanese Unexamined Patent Publication (Kokai) No. 2006-321751, Japanese Unexamined Patent Publication (Kokai) No. 2006-233356, Japanese Unexamined Patent Publication (Kokai) No. 2006-160683, Japanese Unexamined Patent Publication (Kokai) No. 2005-298514, Japanese Unexamined Patent Publication (Kokai) No. 2005-298513, Japanese Unexamined Patent Publication (Kokai) No. 2005-008643, Japanese Unexamined Patent Publication (Kokai) No. 2004-131484 and Japanese Unexamined Patent Publication (Kokai) No. 2003-160439 disclose compositions containing a photoluminescent pigment having an interference function. However, all publications disclose aqueous or oil-based manicures utilizing a lacquer composition and therefore differ from the gel nail type artificial nail composition of the present invention.

SUMMARY OF THE INVENTION

An object of the present invention is to provide an artificial nail composition which can easily impart a special appearance to the tip of the finger, and which is an artificial nail material coated on a natural or artificial nail, and is used by coating on the surface of a natural or artificial nail followed by polymerization and, more particularly, it relates to an artificial nail composition which is vivid and has a natural color tone having a transparent sensation, that cannot be achieved by a conventionally used artificial nail composition containing an organic and/or inorganic colorant utilizing an absorbing and/or scattering phenomenon of light, and imparts special appearance by an interference color.

The present invention provides an artificial nail composition comprising: a component (a): a compound having at least one radical polymerizable unsaturated double bond in the molecule, a component (b): a radical polymerization initiator, a component (c): an organic and/or inorganic colorant utilizing an absorbing and/or scattering phenomenon of light, and a component (d): an inorganic colorant having at least one kind of interference color, wherein an amount of the component (b) is 0.01 to 10 parts by weight, an amount of the component (c) is 0 to 10 parts by weight and an amount of the component (d) is 0.01 to 20 parts by weight with respect to 100 parts by weight of the component (a).

According to the present invention, an organic and/or inorganic colorant having an interference color obtains a vivid color tone by enhancing the reflection of a specific wavelength. Thus it is possible to obtain an artificial nail composition which is vivid and has a natural color tone having a transparent sensation and imparts a special appearance by an interference color. It is also possible to obtain a composition having improved durability and operability over conventionally used oil-based or aqueous manicures utilizing an industrial lacquer composition.

DETAILED DESCRIPTION OF THE INVENTION

Figure 1:
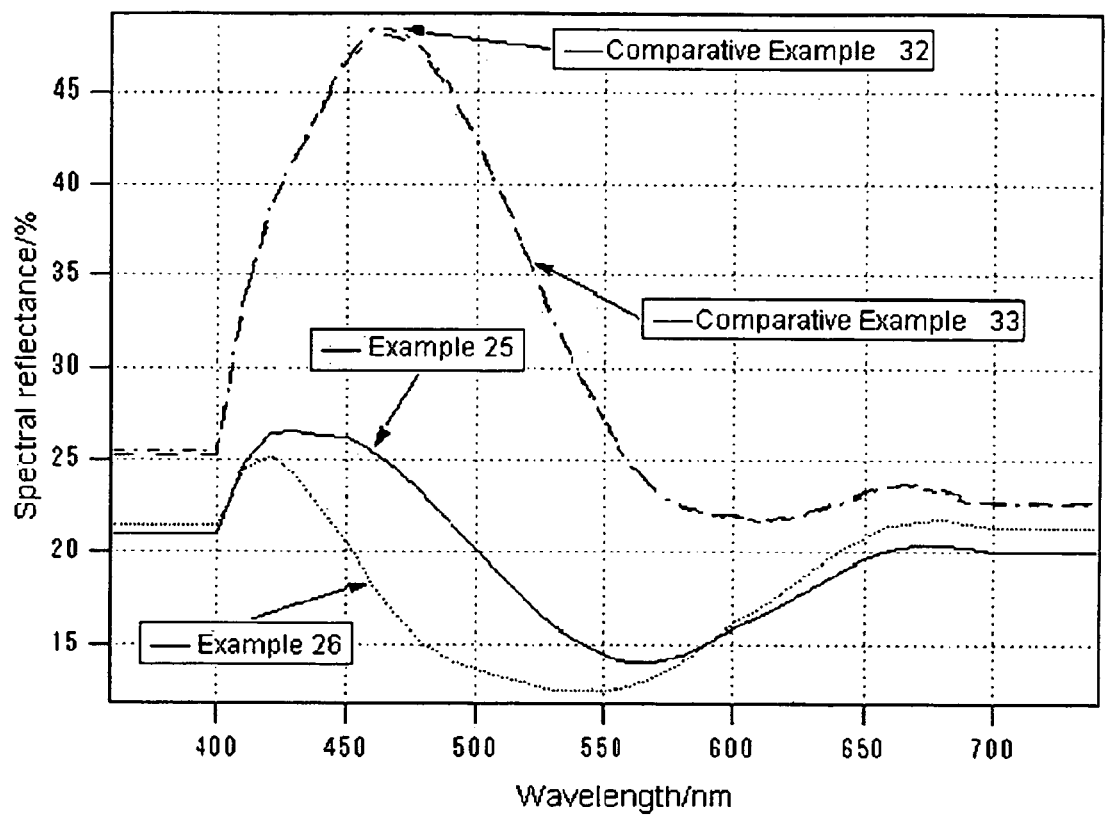
FIG. 1 is a graph showing spectral reflectances with respect to disk-shaped cured bodies formed from compositions of Example 25, Example 26, Comparative Example 32 and Comparative Example 33.
Figure 2:
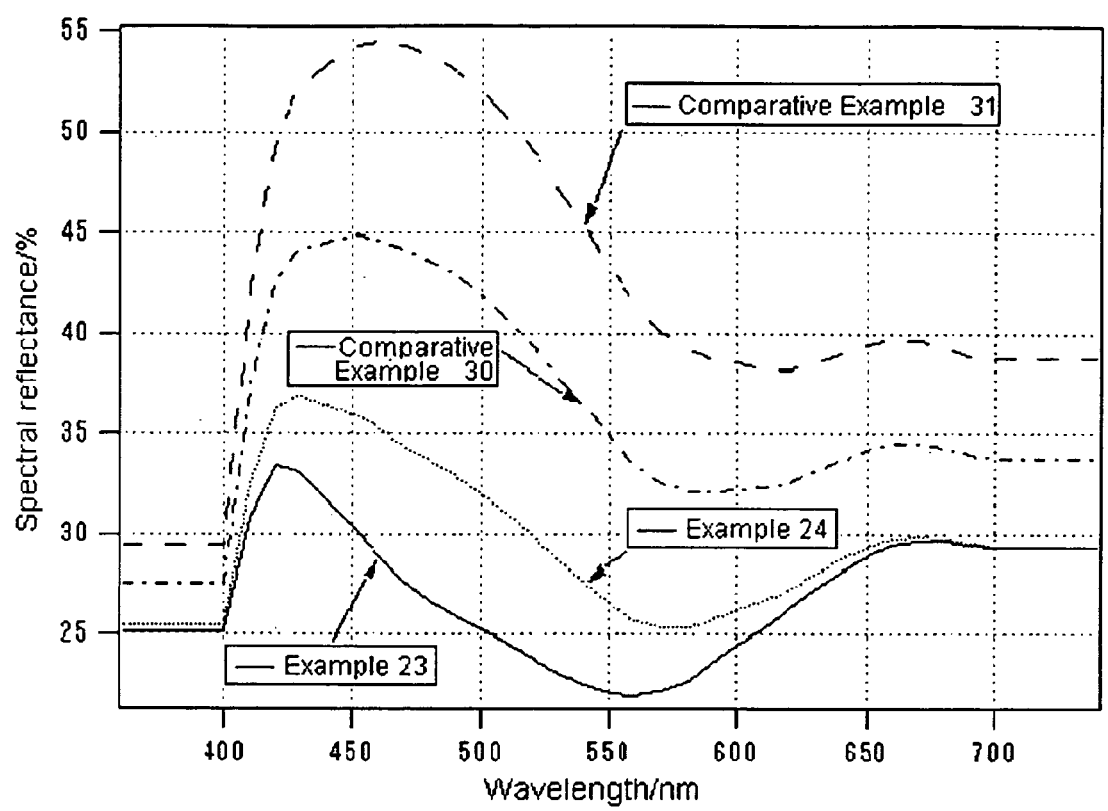
FIG. 2 is a graph showing spectral reflectances with respect to disk-shaped cured bodies formed from compositions of Example 23, Example 24, Comparative Example 30 and Comparative Example 31.
Figure 3:
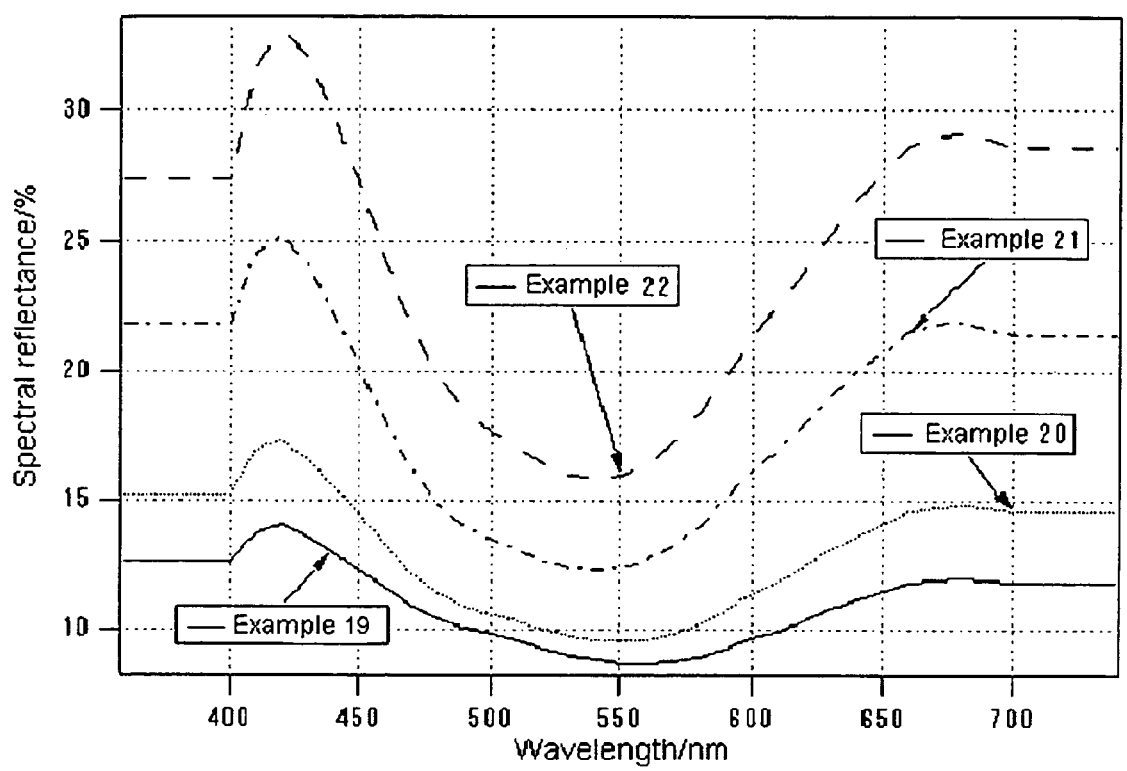
FIG. 3 is a graph showing spectral reflectances with respect to disk-shaped cured bodies formed from compositions of Example 19, Example 20, Example 21 and Example 22.
Figure 4:
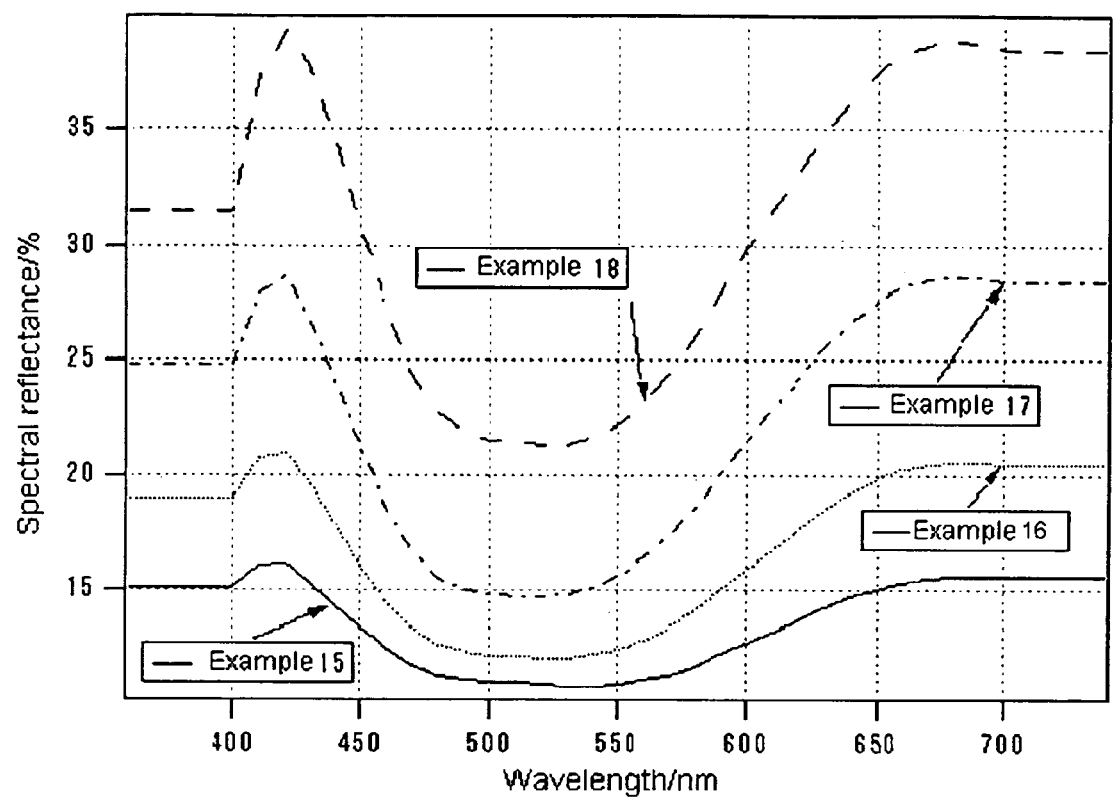
FIG. 4 is a graph showing spectral reflectances with respect to disk-shaped cured bodies formed from compositions of Example 15, Example 16, Example 17 and Example 18.

In the present invention, a compound having at least one radical polymerizable unsaturated double bond in the molecule (a) can be used by selected from known monofunctional and polyfunctional polymerizable monomers. Typical examples of the compound, which is preferably used, include polymerizable monomers having an acryloyl group and/or a methacryloyl group or urethane (meth)acrylates. In the present invention, both an acryloyl group-containing polymerizable monomer and a methacryloyl group- containing polymerizable monomer are comprehensively represented by (meth)acrylate or (meth)acryloyl.

Specific examples thereof include monofunctional monomers such as methoxyethylene glycol (meth)acrylate, methoxypolyethylene glycol (meth)acrylate, phenoxyethylene glycol (meth)acrylate, phenoxypolyethylene glycol (meth) acrylate, 2-hydroxy-3-phenoxypropyl (meth)acrylate, 2-(meth)acryloyloxyethylsuccinic acid, 2-(meth)acryloyloxyethylphthalic acid, 2-(meth)acryloyloxypropylhexaphthalic acid, stearyl(meth)acrylate and 3-chloro-2-hydroxypropyl (meth)acrylate;

difunctional monomers such as 1, 6-hexanediol di(meth) acrylate, 1,9-nonanediol di(meth)acrylate, 1,10-decanediol di(meth)acrylate, neopentyl glycol di(meth)acrylate, 2-methyl-1,8-octanediol di(meth)acrylate, glycerin di(meth)acrylate, ethylene glycol di(meth)acrylate, polyethylene glycol di(meth)acrylate, propylene glycol di(meth)acrylate, polypropylene glycol di(meth)acrylate, ethoxylated polypropylene glycol di(meth)acrylate, ethoxylated propylene glycol di(meth)acrylate, ethoxylated bisphenol A di(meth)acrylate, propoxylated bisphenol A di(meth)acrylate, propoxylated ethoxylated bisphenol A di(meth)acrylate and tricyclodecanedimethanol di(meth)acrylate; and tri- or higher polyfunctional monomers such as trimethylolpropane tri(meth)acrylate, ethoxylated trimethylolpropane tri(meth)acrylate, ethoxylated glycerin tri(meth)acrylate, ditrimethylolpropane tetra(meth)acrylate, pentaerythritol tri(meth)acrylate, pentaerythritol tetra(meth)acrylate, propoxylated pentaerythritol tetra(meth)acrylate, ethoxylated pentaerythritol (meth)acrylate, dipentaerythritol hexa(meth)acrylate and ethoxylated isocyanuric acid tri(meth) acrylate.

Urethane (meth)acrylates used in the present invention have at least two or more of acryloyl groups and/or methacryloyl groups and an urethane group in one molecule. For example, 7,7,9-trimethyl-4,13-dioxo-3,14-dioxo-5,12-diaza-hexadecane-1,16-diol -dimethacrylate (hereinafter, referred to as "UDM"), 1,6-bis[(2-phenoxy-2'-acryloxy)isopropyloxy)carbonylamino]hexane (hereinafter, referred to as "UDMA"), 1,1,1-tri[6-{1-acryloxy-3-phenoxy) isopropyloxycarbanylamino}hexylcarbamoyloxymethyl] propane (hereinafter, referred to as "URO") are included.

In addition to the above-described (meth) acrylate-based polymerizable monomers, other polymerizable monomers, oligomers or polymers of monomers, for example, monomers having at least one polymerizable group in the molecule may be used without any limitation according to the purposes of the artificial nail composition. These monomers may have a substituent such as an acidic group or a fluoro group in the same molecule.

In the present invention, a compound having at least one radical polymerizable unsaturated double bond in the molecule (a) includes not only a single component, but also a mixture of polymerizable monomers. When the polymerizable monomer has very high viscosity at room temperature or is a solid, it is preferred to use as a mixture of a low-viscosity polymerizable monomer and a polymerizable monomer. Not only two or more kinds, but also three or more kinds may be used in combination.

Furthermore, in order to improve adhesion of the artificial nail composition with a natural nail and/or an artificial nail, it is possible to include an acidic compound having at least one radical polymerizable unsaturated double bond in the molecule as a compound having at least one radical polymerizable unsaturated double bond in the molecule (a). Specifically, the acidic compound is a compound having a carboxyl group, a sulfonic acid group or a phosphoric acid group, preferably an acidic phosphorus compound having at least one radical polymerizable unsaturated double bond in the molecule, and particularly preferably a compound having a P—OH bond. Examples of the substituent include a phosphoric acid monoester group, a phosphoric acid diester group, a phosphonic acid group, a phosphonic acid monoester group, a phosphorous acid monoester group, a phosphinic acid group and a pyrophosphoric acid group. Among these groups, a phosphoric acid monoester group, a phosphoric acid diester group and a phosphonic acid group are particularly preferred.

In the present invention, the radical polymerization initiator (b) can be used in an amount within a range from 0.01 to 10 parts by weight, and preferably from 0.1 to 5 parts by weight with respect to 100 parts by weight of the component (a). Also, known thermopolymerization initiators and photopolymerization initiators can be used. Examples of the photopolymerization initiator include benzoinethers, benzylketals, α-dialkoxyacetophenones, α-hydroxyalkylphenones, α-aminoalkylphenone, acylphosphine oxides, benzophenones, thioxanthones and titanocenes. Among these, 2-hydroxy-2-methylpropiophenone and acylphosphine oxides are preferred.

It is also preferred to use the above-described photoinitiator in combination with the photopolymerization accelerator. In particular, when tertiary amines are used as the photopolymerization accelerator, it is more preferred to use a compound in which a nitrogen atom is directly substituted on an aromatic group. It is possible to use, as the photopolymerization accelerator, tertiary amines such as N,N-dimethylaniline, N,N-diethylaniline, N,N-di-n-butylaniline, N,N-dibenzylaniline, N,N-dimethyl-p-toluidine, N,N-dimethyl-m-toluidine, N,N-diethyl-p-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amino ester, N,N-dimethylanthranilic acid methyl ester, N,N-dihydroxyethylaniline, N,N-dihydroxyethyl-p-toluidine, p-dimethylaminophenyl alcohol, p-dimethylaminostyrene,. N,N-dimethyl-3,5-xylidin, 4-dimethylaminopyridine, N,N-dimethyl-a-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate and 2,2'-(n-butylimino) dimethanol; barbituric acids such as 5-butylbarbituric acid and 1-benzyl-5-phenylbarbituric acid, and metal salts thereof such as sodium salts and calcium salts; and tin compounds such as dibutyl-tin-diacetate, dibutyl-tin-dimaleate, dioctyl-tin-dimaleate, dioctyl-tin-dilaurate, dibutyl-tin-dilaurate, dioctyl-tin-diperacetate, dioctyl-tin-S,S'-bis-isooctylmercaptoacetate and tetramethyl-1,3-diacetoxydistanoxane. Among these photopolymerization accelerators, at least one kind can be selected and used, and two or more kinds of them can be used in combination. The amount of the above-described initiators and accelerators can be appropriately decided.

Furthermore, it is effective to add, in addition to tertiary amines, oxycarboxylic acids such as citric acid, malic acid, tartaric acid, glycolic acid, gluconic acid, a-oxyisobutyric acid, 2-hydroxypropanoic acid, 3-hydroxypropanoic acid, 3-hydroxybutanoic acid, 4-hydroxybutanoic acid and dimethylolpropionic acid so as to improve photopolymerization acceleration ability.

Specific examples of the thermopolymerization initiator which can be preferably used include organic peroxides such as benzoyl peroxide, parachlorobenzoyl peroxide, 2,4-dichlorobenzoyl peroxide, acetyl peroxide, lauroyl peroxide, tertiary butyl peroxide, cumen hydroperoxide, 2,5-dimethylhexane-2,5-dihyperoxide, methyl ethyl ketone peroxide and tertiary butylperoxybenzoate; and azo compounds such as azobisisobutyronitrile, methyl azobisisobutyrate and azobiscyanovaleric acid.

The polymerization can also be performed at normal temperature by using the above-described organic peroxide in combination with an amine compound. It is preferred to use, as the amine compound, a secondary or tertiary amine in which an amine group is bonded with an aryl group in view of curing acceleration. For example, N,N-dimethyl-p-toluidine, N,N-dimethylaniline, N,N-β-hydroxyethyl-aniline, N,N-di(β-hydroxyethyl)-aniline, N,N-di(β-hydroxyethyl)-p-toluidine and N-methyl-aniline, N-methyl-p-toluidine are preferred.

It is also preferred to use, in addition to a combination of the organic peroxide and the amine compound, sulfinate or borate in combination. Examples of sulfinates include sodium benzenesulfonate, lithium benzenesulfinate and sodium p-toluenesulfinate. Examples of borates include sodium salts, lithium salts, potassium salts, magnesium salts, tetrabutylammonium salts and tetramethylammonium salts of trialkylphenylboron and trialkyl(p-fluorophenyl)boron (an alkyl group is an n-butyl group, an n-octyl group, n-dodecyl group, etc.) It is also possible to use, as an organometallic polymerization initiator, organoboron compounds capable of reacting with oxygen or water to generate a radical, such as tributylborane and a partial oxide of tributylborane.

In the present invention, examples of the organic and/or inorganic colorant utilizing an absorbing and/or scattering phenomenon of light (c) include organic colorants such as azo-based pigments, phthalocyanine-based pigments and polycyclic pigments; and inorganic colorants, for example, typical white pigments such as titanium oxide, rutile titanium, anatase titanium, zinc oxide, aluminum oxide and zinc sulfide. In the present invention, the organic and/or inorganic colorant utilizing an absorbing and/or scattering phenomenon of light (c) can be used in an amount within a range from 0 to 10 parts by weight with respect to 100 parts by weight of the component (a).

It is possible to use, as the inorganic colorant, yellow iron oxide, color and/or black pigments such as ultramarine blue, blood red, carbon black and graphite in combination. Titanium oxide and aluminum oxide are suited as the inorganic colorant.

Specific examples of the organic colorant include Victoria Pure Blue B, α-Phthalocyanine Blue, β-Phthalocyanine Blue, γ-Phthalocyanine Blue, ϵ-Phthalocyanine Blue, Naphthol Red FRR, Naphthol AS, Naphthol Red, Pyrazolone Red B, BONA Barium Lake, BONA Calcium Lake, BONA Strontium Lake, Magnesium Lake, Rhodamine Y, Thioindigo Violet, Naphthol Red FGR, Quinacridone Magenta, Toluidine Red, Parachlor Red, Hanza Yellow G, Hanza Yellow GR, Disazo Yellow AAMX, Disazo Yellow AAOT, Vulcan Fast Yellow 5G, Arylide Yellow NCG, Flavanthron Yellow, Strontium Yellow and Antimony Yellow. In particular, as a combination of color organic colorants, for example, Pigment Blue 15:2 (α-Phthalocyanine Blue) is suited as a blue organic colorant, Pigment Red 48:2 (BONA Calcium Lake) is suited as a red organic colorant, and Pigment Yellow 14 (Diazo Yellow AAOT) is suited as a yellow colorant.

In the present invention, the inorganic colorant having at least one kind of an interference color (d) is a colorant capable of developing a different color due to the fact that since light travels in a wave form, the light reflected by the surface when light contacts a thin film having a thickness which is nearly equal to the wavelength of visible rays interferes with the light reflected by the inside or reflected on the back surface and thus causes amplification or cancellation. In the present invention, the inorganic colorant having at least one kind of an interference color (d) can be used in an amount within a range from 0 to 10 parts by weight, and preferably from 0.01 to 20 parts by weight with respect to 100 parts by weight of the component (a).

Specifically, the inorganic colorant having an interference color is an inorganic colorant having an interference color in which an anatase type titanium oxide, a rutile type titanium oxide, a pseudobrookite type titanium oxide or tin oxide are uniformly coated on a base material such as a glass flake or aluminum oxide. An inorganic colorant comprising an aluminum oxide as the base material, and titanium oxide and tin oxide coated on the aluminum oxide is particularly preferred.

In the present invention, a contrast ratio gives a measure of transparency. The contrast ratio is a measure of transparency and is calculated using a Y value relating to brightness in a tristimulus value of a XYZ color system determined by JIS Z8701. Specifically, a black background or a white background is contacted with a 200 μm cured artificial nail composition. Standard light C is irradiated, and a Y value in the reflected light is read. The contrast ratio (C) is determined from Yb/Yw where Yb denotes Y having a black background and Yw denotes Y having a white background. As the value C approaches 1, the cured body approaches an opaque cured body, while as the value C approaches 0, the cured body approaches a transparent cured body.

EXAMPLES

The present invention will be described in detail by way of Examples, but the invention is not limited to the following Examples.
Abbreviations of Compounds used in Examples of the Present Invention
(a) Compound having at least one radical polymerizable unsaturated double bond in the molecule
UDMA: dimethacryloxyethyl-2,2,4-trimethylhexamethylene diurethane
BisGMA: bisphenol A-diglycidyl methacrylate
14G: tetradecaethylene glycol dimethacrylate
BisMEP: bis[2-(methacryloxy)ethyl]phosphate
4AET: 4-acryloxyethyltrimellitic acid
(b) Radical Polymerization Initiator
MAPO: 2,4,6-trimethylbenzoyl-diphenyl-phosphine oxide
DAR1173: 2-hydroxy-2-methyl-l-phenyl-propan-1-one
IRG184: 1-hydroxy-cyclohexyl-phenyl-ketone
(c) Organic and/or Inorganic Colorant Utilizing an Absorbing and/or Scattering Phenomenon of Light
Blue 5050A: Fastogen Blue 5050A (manufactured by Dainippon Ink and Chemicals, Incorporated.)
Red 3013: Symuler Red 3013 (manufactured by Dainippon Ink and Chemicals, Incorporated.)
Yellow 5GF: Symuler Fast Yellow 5GF (manufactured by Dainippon Ink and Chemicals, Incorporated.)
JR-805: titanium dioxide (manufactured by TAYCA Corporation)
(d) Inorganic Colorant Having at Least One Kind of Interference Color
T60-23: Xirallic T60-23WNT (manufactured by Merck Ltd.)
T60-21: Xirallic T60-21WNT (manufactured by Merck Ltd.)
Other Additives
R974: ultrafine silica particles (manufactured by NIPPON AEROSIL CO., LTD.)
Equipment and Apparatus used in Examples of the Present Invention
Ultraviolet polymerization apparatus: AKZENTZ UV LAMP (Model UVL-92, manufactured by Takigawa Co., Ltd.)
Spectrophotometer: CM-2002 (manufactured by Konica Minolta Holdings, Inc.)

Methods for preparation of materials and evaluation methods used in Examples of the present invention will be described below.
Method for Preparation of Artificial Nail Composition Raw materials (a) and (b) were weighed in accordance with the formulation shown in Table 1., mixed under atmospheric pressure at 60° C. for 3 hours and then mixed under atmospheric pressure at 23° C. for 12 hours. Raw materials (c) and (d), and additives were weighed and then additive raw materials were dispersed using an autorotation/revolution type mixer. After degassing under 40 to 45 Torr, a high-viscosity transparent liquid was obtained.
Method for Production of Cured Artificial Nail Composition for Colorimetry A ring type stainless steel mold having measuring 30 mm in diameter (inner diameter) and 200 μm in thickness was filled with the artificial nail composition. The shape was modified and the surface to be irradiated with light was shielded from air by pressure welding using glass in a vertical direction. Using an ultraviolet polymerization apparatus (AKZENTZ UV LAMP), photopolymerization of upper and lower surfaces was performed for 3 minutes respectively to produce a disk-shaped cured body of the artificial nail composition. This resultant disk-shaped cured body was used as a disk-shaped specimen for colorimetry.
Colorimetry Method Colorimetry was performed in accordance with JIS Z8722: 2000. The measurement conditions are described below.
a) Illuminant and color system: An auxiliary illuminant was used and an XYZ color system was used.
b) The measurement was carried out by a reflection measuring method.
c) Geometrical/optical conditions defined in JIS Z 8722 used for measurement: Conditions c [8/0]
d) Model and name of test apparatus: Spectrophotometer (Model CM-2002, manufactured by Konica Minolta Holdings, Inc.)
e) Back surface of specimen: Optical trap free from transmissiveness and internal reflection was used.

From the resultant XYZ values, CIE1976ab chroma (may be abbreviated to C* in this Example) was obtained by a calculation formula described in JIS Z8729:2004. The resultant CIE1976ab chroma is shown in Table 1.

Furthermore, spectral reflectance graphs obtained under the colorimetric conditions are shown in FIGS. 1 to 15.
Calculation of Contrast Ratio In the present invention, a contrast ratio gives a measure of transparency. The contrast ratio is a measure of transparency and is calculated by a Y value relating to brightness in the tristimulus values of a XYZ color system. Specifically, a black background or a white background is contacted with a 200 μm thick cured artificial nail composition, standard light C is irradiated and the Y value in reflected light is read. The contrast ratio (C) is determined from Yb/Yw where Yb denotes Y having a black background and Yw denotes Y having a white background. As the value C approaches 1, the cured body approaches an opaque cured body, while as the value C approaches 0, the cured body approaches a transparent cured body. The resultant contrast ratio is shown in Table 1.

As is apparent from the results shown in FIG. 8, FIG. 9, FIG. 10 and FIG. 7, in Examples 1 to 12, spectra of spectral reflectances each having a peak at about 450 nm were obtained and the resultant cured compositions were cured compositions each having a blue interference color. The cured compositions of Examples 1 to 12 developed a violetish red and were excellent in appearance.

Figure 7:
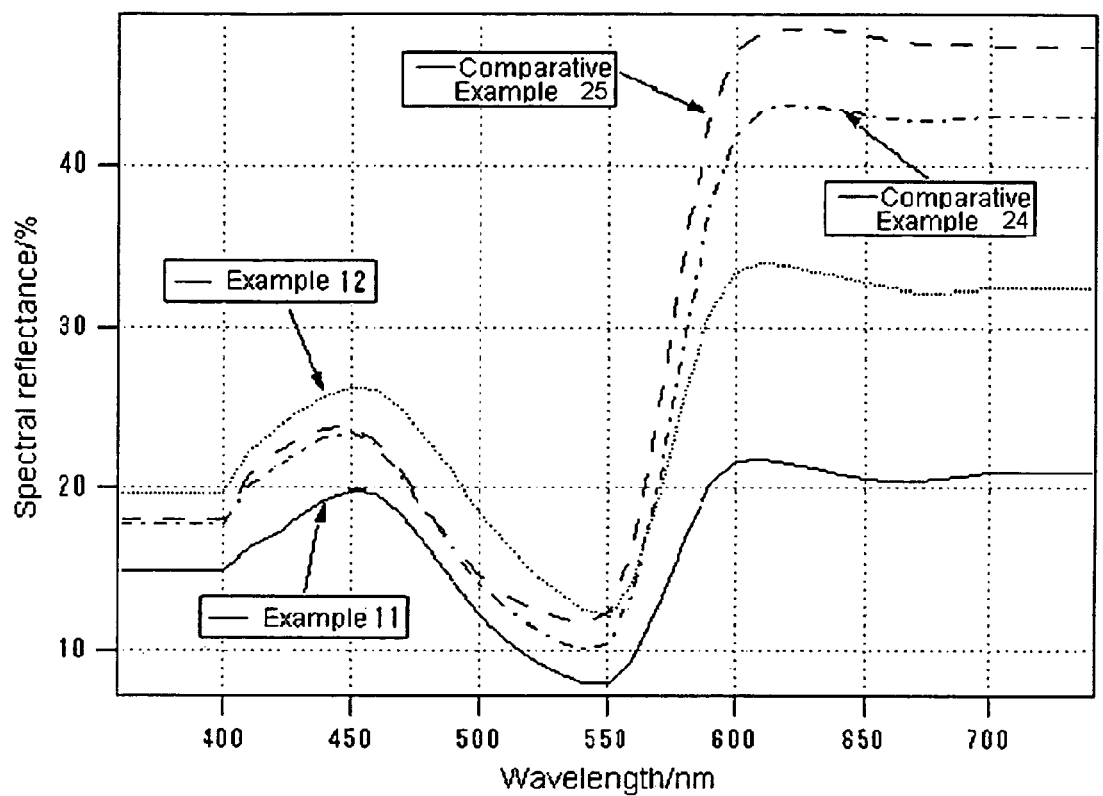
FIG. 7 is a graph showing spectral reflectances with respect to disk-shaped cured bodies formed from compositions of Example 11, Example 12, Comparative Example 24 and Comparative Example 25.
Figure 8:
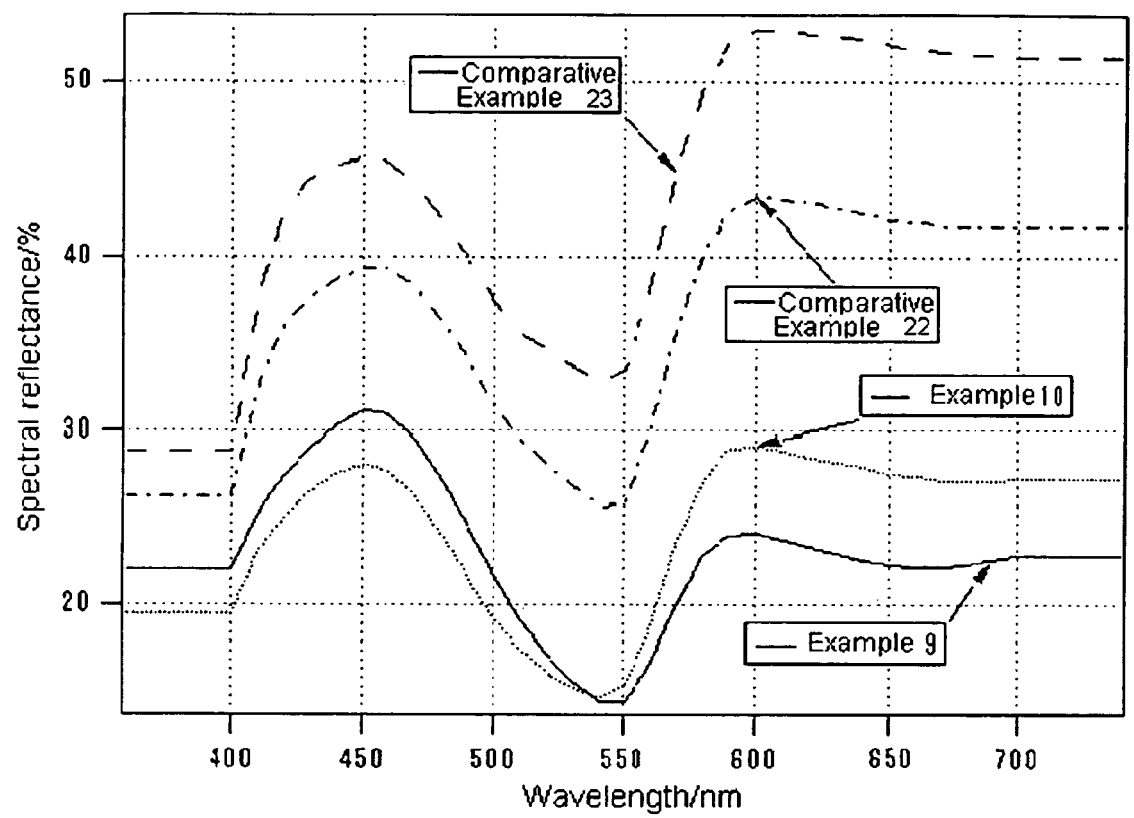
FIG. 8 is a graph showing spectral reflectances with respect to disk-shaped cured bodies formed from compositions of Example 9, Example 10, Comparative Example 22 and Comparative Example 23.
Figure 9:
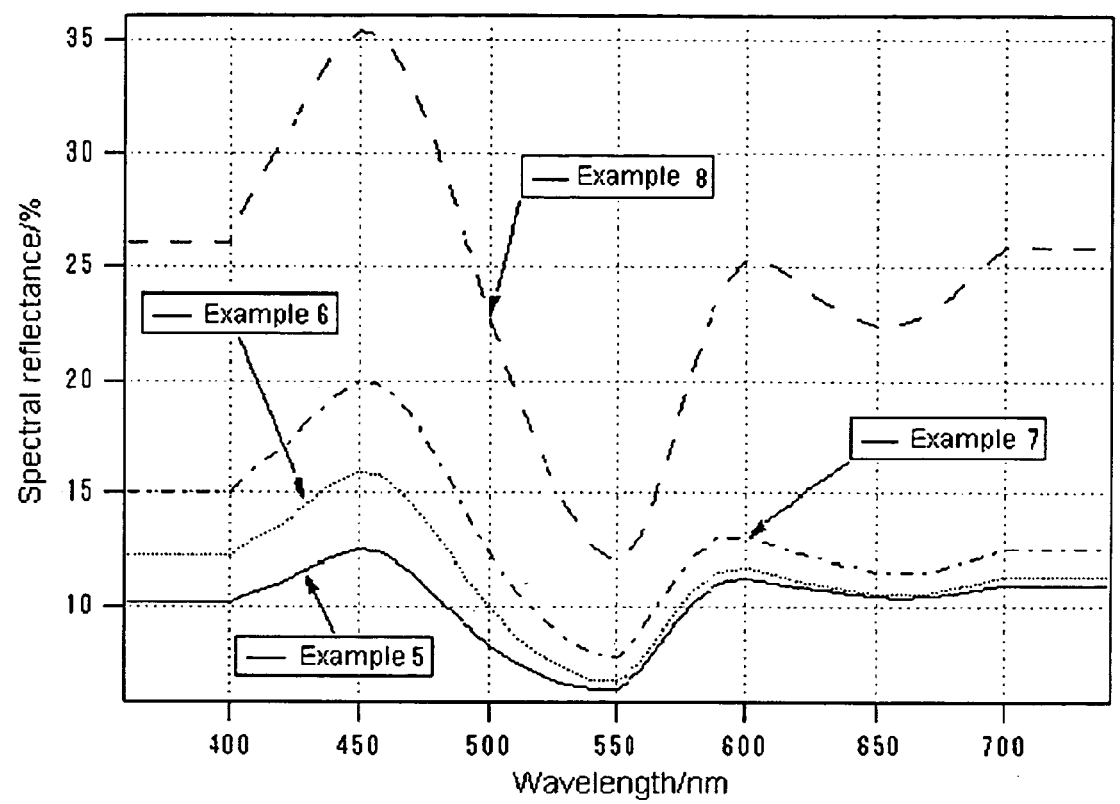
FIG. 9 is a graph showing spectral reflectances with respect to disk-shaped cured bodies formed from compositions of Example 5, Example 6, Example 7 and Example 8.
Figure 10:
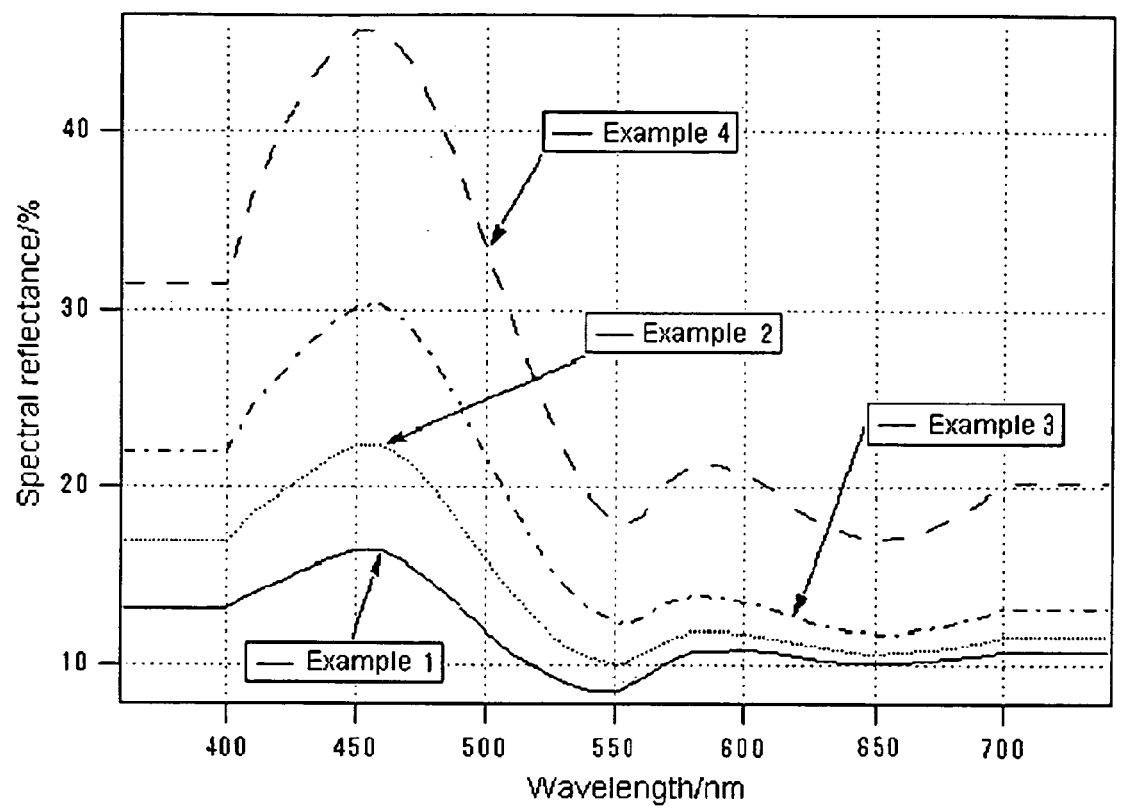
FIG. 10 is a graph showing spectral reflectances with respect to disk-shaped cured bodies formed from compositions of Example 1, Example 2, Example 3 and Example 4.
Figure 11:
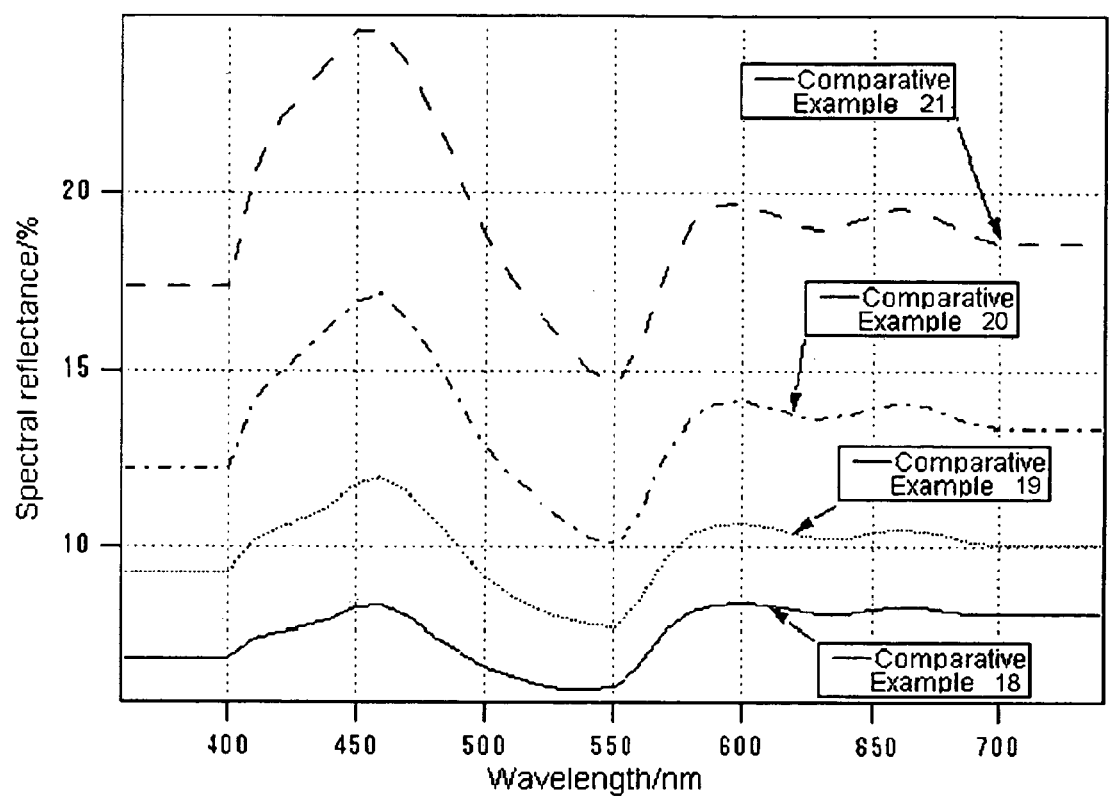
FIG. 11 is a graph showing spectral reflectances with respect to disk-shaped cured bodies formed from compositions of Comparative Example 18, Comparative Example 19, Comparative Example 20 and Comparative Example 21.
Figure 12:
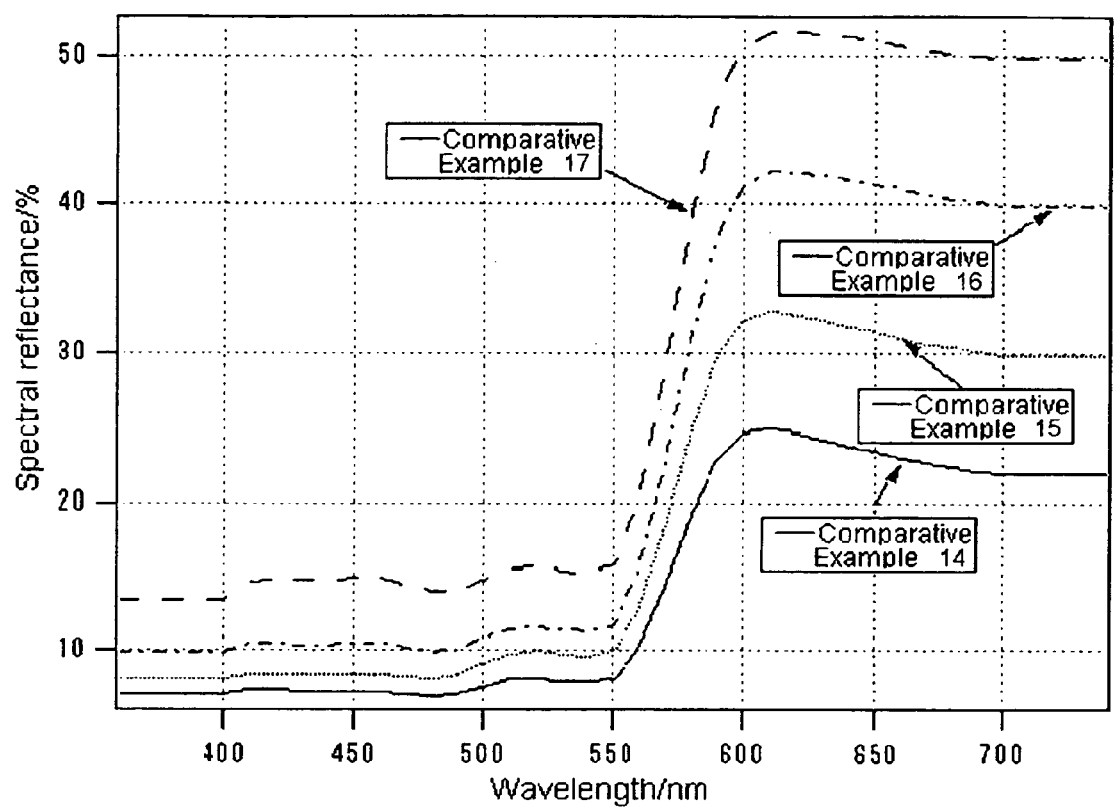
FIG. 12 is a graph showing spectral reflectances with respect to disk-shaped cured bodies formed from compositions of Comparative Example 14, Comparative Example 15, Comparative Example 16 and Comparative Example 17.
Figure 13:
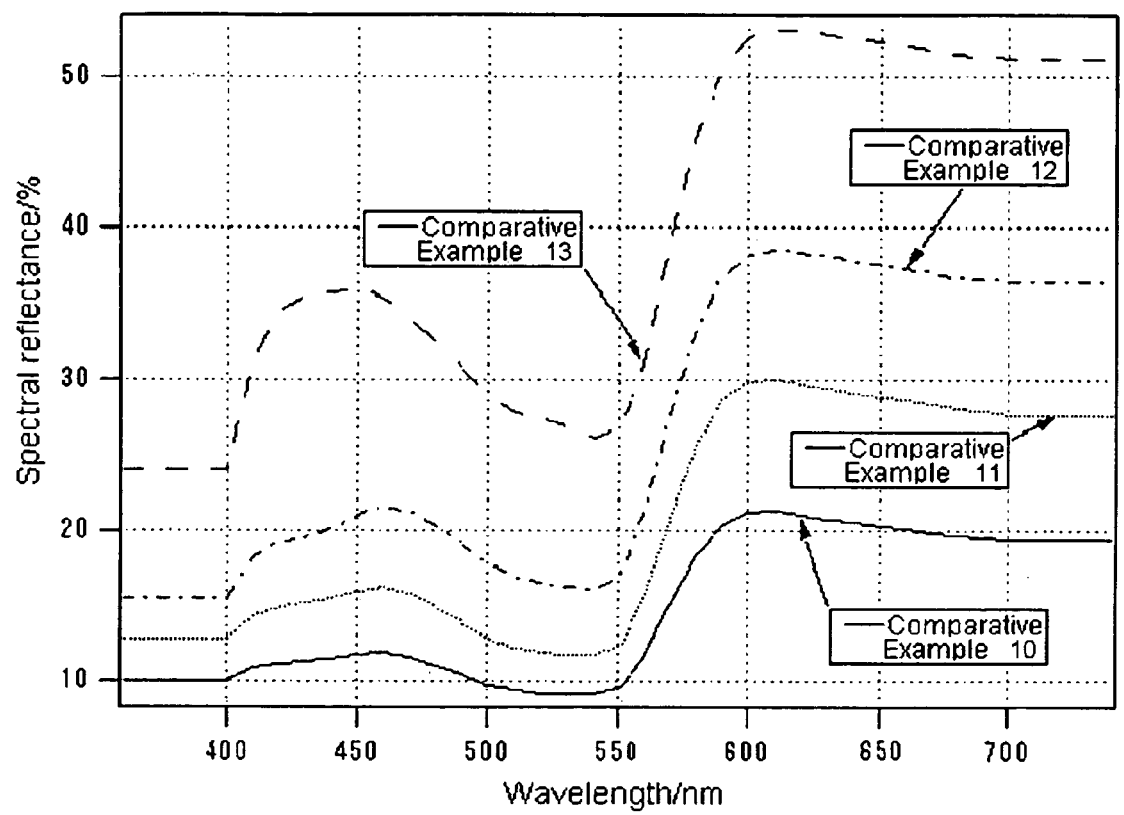
FIG. 13 is a graph showing spectral reflectances with respect to disk-shaped cured bodies formed from compositions of Comparative Example 10, Comparative Example 11, Comparative Example 12 and Comparative Example 13.
Figure 14:
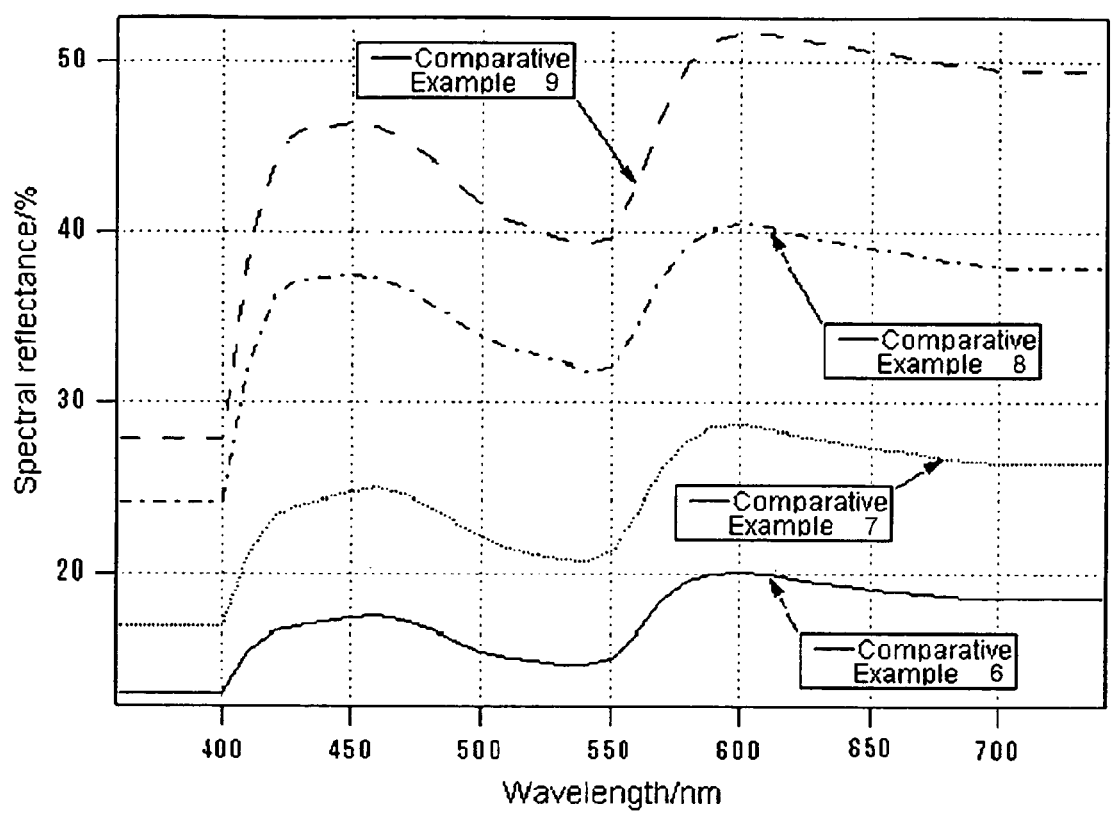
FIG. 14 is a graph showing spectral reflectances with respect to disk-shaped cured bodies formed from compositions of Comparative Example 6, Comparative Example 7, Comparative Example 8 and Comparative Example 9.
Figure 15:
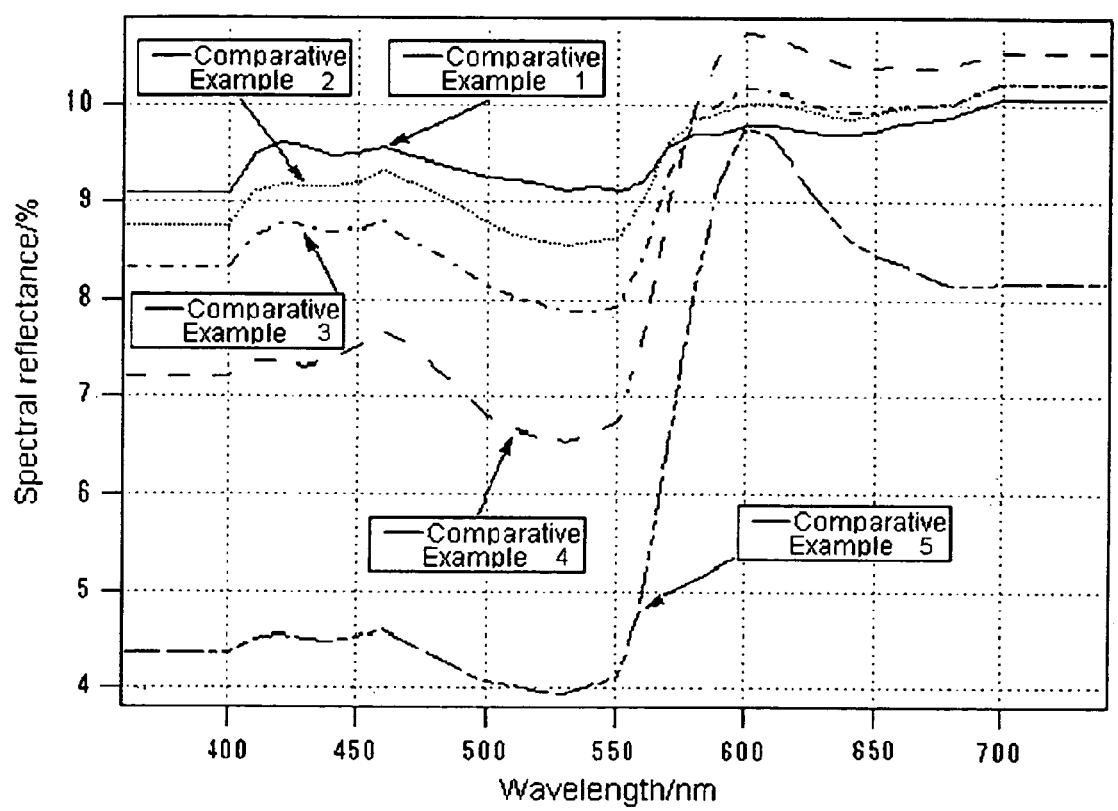
FIG. 15 is a graph showing spectral reflectances with respect to disk-shaped cured bodies formed from compositions of Comparative Example 1, Comparative Example 2, Comparative Example 3, Comparative Example 4 and Comparative Example 5.

As is apparent from the results shown in FIG. 7 and FIG. 8, in Comparative Examples 22 to 25, spectra of spectral reflectances each having a peak at about 450 nm were obtained and the resultant cured compositions were cured compositions each having a blue interference color. However, as is apparent from the results shown in Table 1, a contrast ratio of the cured compositions was 0.6 or more and an interference color giving beautiful appearance was decreased by scattering caused by the component (c), and the resultant cured compositions were inferior in appearance.

Figure 6:
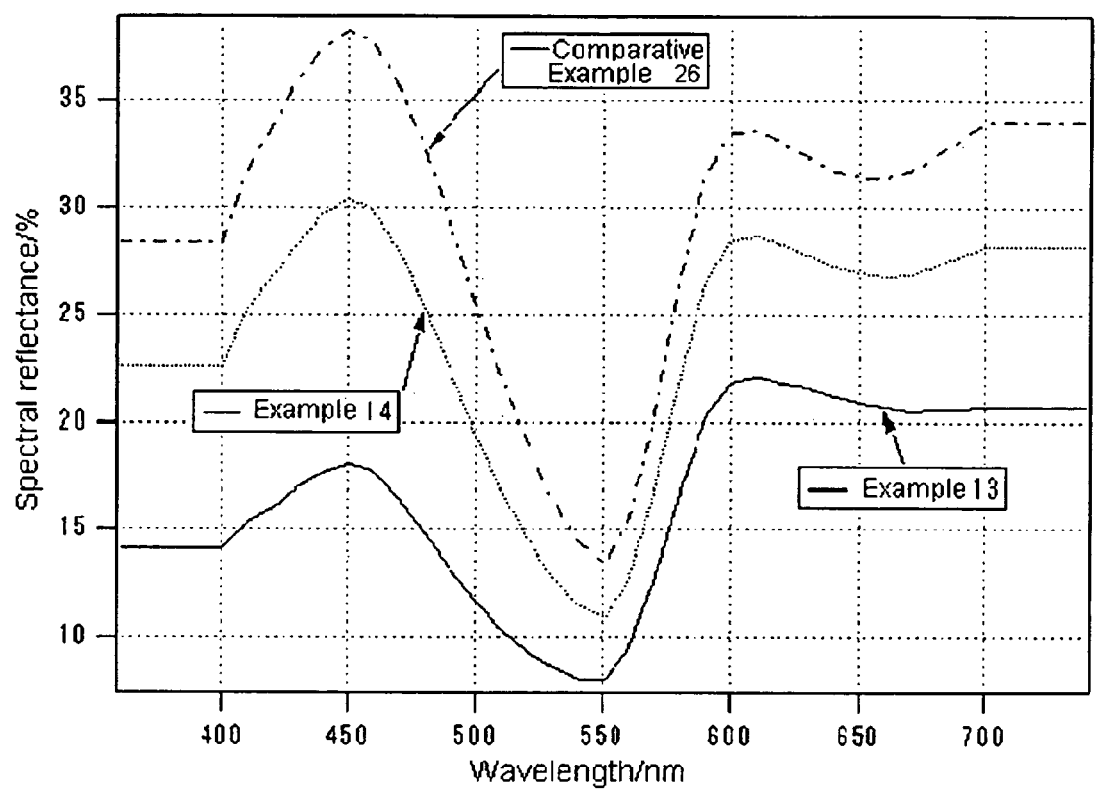
FIG. 6 is a graph showing spectral reflectances with respect to disk-shaped cured bodies formed from compositions of Example 13, Example 14 and Comparative Example 26.

Similarly, as is apparent from the results shown in FIG. 6, in Examples 13 to 14, spectra of spectral reflectances each having a peak at about 450 nm were obtained and the resultant cured compositions were cured compositions each having a blue interference color. The cured compositions of Examples 13 to 14 developed a violetish red and were excellent in appearance.

Figure 5:
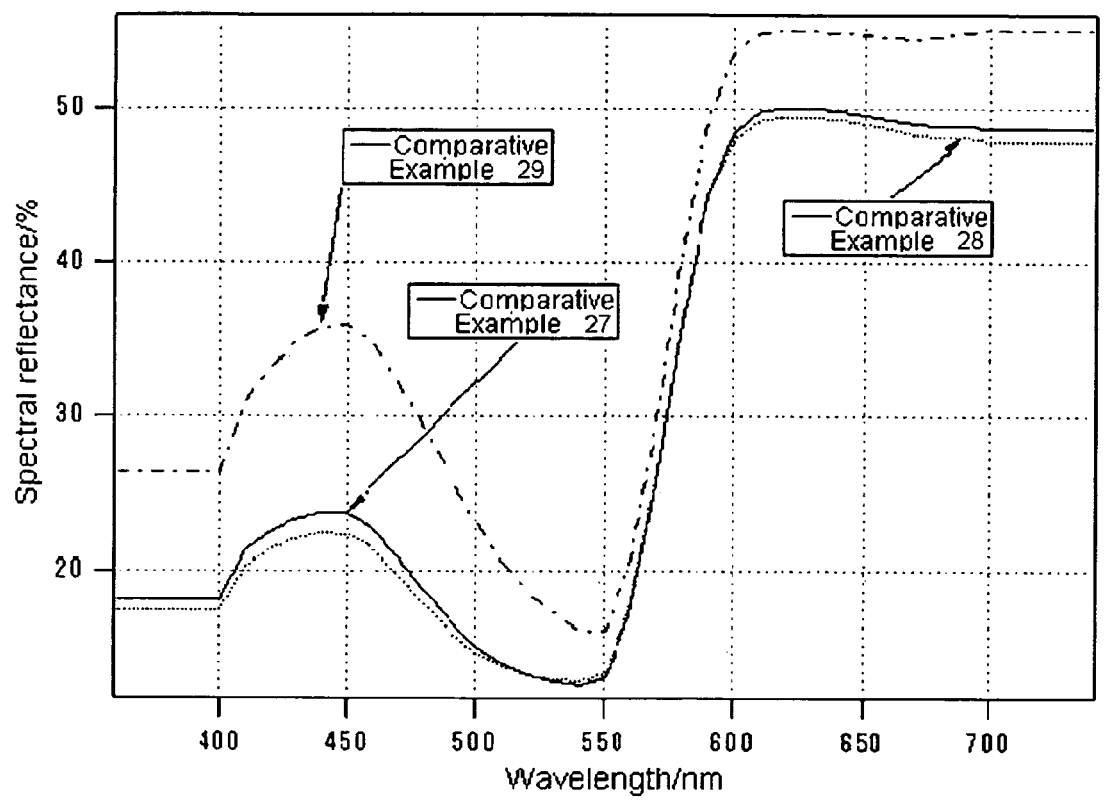
FIG. 5 is a graph showing spectral reflectances with respect to disk-shaped cured bodies formed from compositions of Comparative Example.27, Comparative Example 28 and Comparative Example 29.

However, as is apparent from the results shown in FIG. 5 and FIG. 6, in Comparative Examples 26 to 29, spectra of spectral reflectances each having a peak at about 450 nm were obtained and the resultant cured compositions were cured compositions each having a blue interference color. However, as is apparent from the results shown in Table 1, a contrast ratio of the cured compositions was 0.6 or more and an interference color giving beautiful appearance was decreased by scattering caused by the component (c), and the resultant cured compositions were inferior in appearance.

The compositions of Comparative Examples 1 to 21 are compositions containing no component (d). As is apparent from the results shown in FIGS. 11 to 15, spectral reflectances with a color tone derived from the component (d) were obtained. When compared with the cured compositions containing a component (d) of Examples, as is apparent from the results shown in Table 1, the compositions showed low CIE1976ab chroma at the same contrast ratio and were inferior in appearance because a vivid color was not obtained.

As is apparent from the results shown in FIGS. 1 to 4, in Examples 15 to 26, the spectra of spectral reflectances each having a peak at about 610 to 750 nm were obtained and the resultant cured compositions were cured compositions each having a red interference color. The cured compositions of Examples 15 to 26 were excellent in appearance.

However, in Comparative Examples 30 to 33, spectra of spectral reflectances each having a broad peak at about 610 to 750 nm were obtained and the resultant cured compositions were cured compositions each having a red interference color. As is apparent from the results shown in Table 1, a contrast ratio of the cured compositions was 0.6 or more and an interference color giving beautiful appearance was decreased by scattering caused by the component (c), and the resultant cured compositions were inferior in appearance.

TABLE 1

|  | Component (b) | | | Component (a) | | | | | Filler |
| --- | --- | --- | --- | --- | --- | --- | --- | --- | --- |
|  | MAPO | DAR 1173 | IRG 184 | UDMA | BisGMA | 14EG | BisMEP | 4AET | R972 |
| Comparative Example 1 | 1.28 |  |  | 25.64 | 12.82 | 51.27 | 5.13 | 2.56 | 1.28 |
| Comparative Example 2 | 0.74 |  |  | 29.62 | 14.81 | 44.43 | 5.92 | 2.96 | 1.48 |
| Comparative Example 3 | 0.50 |  |  | 30.13 | 15.06 | 40.17 | 8.03 | 4.02 | 2.01 |
| Comparative Example 4 | 0.42 | 0.42 |  | 16.78 | 8.39 | 50.34 | 13.42 | 6.71 | 3.36 |
| Comparative Example 5 | 0.34 | 0.34 |  | 26.94 | 13.47 | 53.88 | 2.69 | 1.35 | 0.67 |
| Comparative Example 6 | 0.34 | 0.34 |  | 41.33 | 20.66 | 27.55 | 5.51 | 2.76 | 1.38 |
| Comparative Example 7 | 0.49 |  | 0.49 | 19.76 | 19.76 | 39.52 | 7.90 | 7.90 | 3.95 |
| Comparative Example 8 | 0.33 |  | 0.33 | 26.56 | 19.92 | 39.83 | 10.62 | 1.33 | 0.66 |
| Comparative Example 9 | 0.31 |  | 0.31 | 36.96 | 6.16 | 49.29 | 2.46 | 2.46 | 1.23 |
| Comparative Example 10 | 1.40 |  |  | 13.96 | 20.94 | 55.84 | 5.58 | 1.40 | 0.70 |
| Comparative Example 11 | 1.75 |  |  | 34.99 | 8.75 | 34.99 | 14.00 | 3.50 | 1.75 |
| Comparative Example 12 | 1.26 |  |  | 37.79 | 12.60 | 37.79 | 2.52 | 5.04 | 2.52 |
| Comparative Example 13 | 0.69 | 0.69 |  | 13.77 | 13.77 | 55.07 | 11.01 | 2.75 | 1.38 |
| Comparative Example 14 | 0.78 | 0.78 |  | 31.12 | 23.34 | 31.12 | 3.11 | 6.22 | 3.11 |
| Comparative Example 15 | 0.70 | 0.70 |  | 41.74 | 6.96 | 41.74 | 5.57 | 1.39 | 0.70 |
| Comparative Example 16 | 0.81 |  | 0.81 | 16.28 | 24.41 | 48.83 | 3.26 | 3.26 | 1.63 |
| Comparative Example 17 | 0.65 |  | 0.65 | 26.02 | 6.51 | 52.05 | 5.20 | 5.20 | 2.60 |
| Comparative Example 18 | 0.71 |  | 0.71 | 42.38 | 14.13 | 28.25 | 11.30 | 1.41 | 0.71 |
| Comparative Example 19 | 1.28 |  |  | 25.51 | 12.75 | 51.02 | 5.10 | 2.55 | 1.28 |
| Comparative Example 20 | 0.74 |  |  | 29.42 | 14.71 | 44.13 | 5.88 | 2.94 | 1.47 |
| Comparative Example 21 | 0.50 |  |  | 29.82 | 14.91 | 39.76 | 7.95 | 3.98 | 1.99 |

|  | Component (c) | | | | Component (d) | | | |
| --- | --- | --- | --- | --- | --- | --- | --- | --- |
|  | Red 3013 | Yellow 5GF | Blue 5050A | JR-805 | T60-23 | T60-21 | Contrast ratio | C* |
| Comparative Example 1 | 0.02 |  |  |  |  |  | 0.11 | 1.46 |
| Comparative Example 2 | 0.04 |  |  |  |  |  | 0.12 | 3.00 |
| Comparative Example 3 | 0.08 |  |  |  |  |  | 0.14 | 4.81 |
| Comparative Example 4 | 0.16 |  |  |  |  |  | 0.16 | 8.92 |
| Comparative Example 5 | 0.32 |  |  |  |  |  | 0.18 | 14.70 |
| Comparative Example 6 | 0.02 |  |  | 0.10 |  |  | 0.26 | 7.26 |
| Comparative Example 7 | 0.02 |  |  | 0.20 |  |  | 0.35 | 8.22 |
| Comparative Example 8 | 0.02 |  |  | 0.40 |  |  | 0.52 | 7.43 |
| Comparative Example 9 | 0.02 |  |  | 0.79 |  |  | 0.66 | 9.22 |
| Comparative Example 10 | 0.08 |  |  | 0.10 |  |  | 0.31 | 18.36 |
| Comparative Example 11 | 0.08 |  |  | 0.20 |  |  | 0.41 | 22.15 |
| Comparative Example 12 | 0.08 |  |  | 0.40 |  |  | 0.55 | 22.53 |
| Comparative Example 13 | 0.08 |  |  | 0.79 |  |  | 0.73 | 21.51 |

TABLE 1-continued

| | | | | | | | |
|---|---|---|---|---|---|---|---|
| Comparative Example 14 | 0.16 | 0.16 | | 0.10 | | 0.41 | 29.02 |
| Comparative Example 15 | 0.16 | 0.16 | | 0.20 | | 0.50 | 34.12 |
| Comparative Example 16 | 0.16 | 0.16 | | 0.40 | | 0.61 | 38.52 |
| Comparative Example 17 | 0.16 | 0.16 | | 0.79 | | 0.74 | 38.00 |
| Comparative Example 18 | 0.16 | | 0.16 | 0.10 | | 0.48 | 7.75 |
| Comparative Example 19 | 0.16 | | 0.16 | 0.20 | | 0.63 | 9.75 |
| Comparative Example 20 | 0.16 | | 0.16 | 0.40 | | 0.85 | 12.90 |
| Comparative Example 21 | 0.16 | | 0.16 | 0.79 | | 0.94 | 14.34 |

| | Component (b) | | | Component (a) | | | | | Filler |
|---|---|---|---|---|---|---|---|---|---|
| | MAPO | DAR 1173 | IRG 184 | UDMA | BisGMA | 14EG | BisMEP | 4AET | R972 |
| Example 1 | 0.42 | 0.42 | | 16.73 | 8.37 | 50.20 | 13.39 | 6.69 | 3.35 |
| Example 2 | 0.34 | 0.34 | | 26.80 | 13.40 | 53.60 | 2.68 | 1.34 | 0.67 |
| Example 3 | 0.34 | 0.34 | | 40.71 | 20.36 | 27.14 | 5.43 | 2.71 | 1.36 |
| Example 4 | 0.48 | | 0.48 | 19.18 | 19.18 | 38.36 | 7.67 | 7.67 | 3.84 |
| Example 5 | 0.33 | | 0.33 | 26.52 | 19.89 | 39.78 | 10.61 | 1.33 | 0.66 |
| Example 6 | 0.31 | | 0.31 | 36.91 | 6.15 | 49.22 | 2.46 | 2.46 | 1.23 |
| Example 7 | 1.37 | | | 13.74 | 20.62 | 54.98 | 5.50 | 1.37 | 0.69 |
| Example 8 | 1.70 | | | 33.95 | 8.49 | 33.95 | 13.58 | 3.39 | 1.70 |
| Example 9 | 1.24 | | | 37.33 | 12.44 | 37.33 | 2.49 | 4.98 | 2.49 |
| Example 10 | 0.68 | 0.68 | | 13.64 | 13.64 | 54.55 | 10.91 | 2.73 | 1.36 |
| Comparative Example 22 | 0.77 | 0.77 | | 30.63 | 22.97 | 30.63 | 3.06 | 6.13 | 3.06 |
| Comparative Example 23 | 0.68 | 0.68 | | 40.96 | 6.83 | 40.96 | 5.46 | 1.37 | 0.68 |
| Example 11 | 0.80 | | 0.80 | 16.09 | 24.14 | 48.28 | 3.22 | 3.22 | 1.61 |
| Example 12 | 0.65 | | 0.65 | 25.81 | 6.45 | 51.62 | 5.16 | 5.16 | 2.58 |
| Comparative Example 24 | 0.69 | | 0.69 | 41.65 | 13.88 | 27.77 | 11.11 | 1.39 | 0.69 |
| Comparative Example 25 | 1.25 | | | 25.00 | 12.50 | 50.00 | 5.00 | 2.50 | 1.25 |
| Example 13 | 0.73 | | | 29.32 | 14.66 | 43.98 | 5.86 | 2.93 | 1.47 |
| Example 14 | 0.49 | | | 29.14 | 14.57 | 38.86 | 7.77 | 3.89 | 1.94 |
| Comparative Example 26 | 0.39 | 0.39 | | 15.76 | 7.88 | 47.27 | 12.61 | 6.30 | 3.15 |

| | Component (c) | | | | Component (d) | | | |
|---|---|---|---|---|---|---|---|---|
| | Red 3013 | Yellow 5GF | Blue 5050A | JR-805 | T60-23 | T60-21 | Contrast ratio | C* |
| Example 1 | 0.04 | | | | 0.40 | | 0.15 | 16.34 |
| Example 2 | 0.04 | | | | 0.79 | | 0.18 | 21.54 |
| Example 3 | 0.04 | | | | 1.57 | | 0.24 | 26.35 |
| Example 4 | 0.04 | | | | 3.10 | | 0.39 | 30.42 |
| Example 5 | 0.16 | | | | 0.40 | | 0.20 | 16.49 |
| Example 6 | 0.16 | | | | 0.79 | | 0.21 | 20.82 |
| Example 7 | 0.16 | | | | 1.57 | | 0.24 | 23.63 |
| Example 8 | 0.15 | | | | 3.10 | | 0.48 | 32.12 |
| Example 9 | 0.04 | | | 0.10 | 1.57 | | 0.37 | 22.95 |
| Example 10 | 0.04 | | | 0.20 | 1.57 | | 0.40 | 20.79 |
| Comparative Example 22 | 0.04 | | | 0.39 | 1.57 | | 0.61 | 17.18 |
| Comparative Example 23 | 0.04 | | | 0.78 | 1.56 | | 0.72 | 16.08 |
| Example 11 | 0.16 | | | 0.10 | 1.57 | | 0.36 | 26.77 |
| Example 12 | 0.16 | | | 0.20 | 1.57 | | 0.57 | 27.16 |
| Comparative Example 24 | 0.16 | | | 0.39 | 1.57 | | 0.66 | 36.46 |
| Comparative Example 25 | 0.16 | | | 0.78 | 1.56 | | 0.68 | 36.55 |
| Example 13 | 0.16 | | | 0.10 | 0.79 | | 0.35 | 25.03 |
| Example 14 | 0.15 | | | 0.10 | 3.09 | | 0.51 | 30.89 |
| Comparative Example 26 | 0.15 | | | 0.09 | 6.00 | | 0.60 | 32.25 |

| | Component (b) | | | Component (a) | | | | | Filler |
|---|---|---|---|---|---|---|---|---|---|
| | MAPO | DAR 1173 | IRG 184 | UDMA | BisGMA | 14EG | BisMEP | 4AET | R972 |
| Comparative Example 27 | 0.33 | 0.33 | | 26.56 | 13.28 | 53.12 | 2.66 | 1.33 | 0.66 |
| Comparative Example 28 | 0.33 | 0.33 | | 39.73 | 19.86 | 26.48 | 5.30 | 2.65 | 1.32 |
| Comparative Example 29 | 0.46 | | 0.46 | 18.44 | 18.44 | 36.89 | 7.38 | 7.38 | 3.69 |
| Example 15 | 0.33 | | 0.33 | 26.55 | 19.91 | 39.82 | 10.62 | 1.33 | 0.66 |
| Example 16 | 0.31 | | 0.31 | 36.96 | 6.16 | 49.28 | 2.46 | 2.46 | 1.23 |
| Example 17 | 1.38 | | | 13.76 | 20.64 | 55.04 | 5.50 | 1.38 | 0.69 |
| Example 18 | 1.70 | | | 33.99 | 8.50 | 33.99 | 13.59 | 3.40 | 1.70 |
| Example 19 | 1.26 | | | 37.76 | 12.59 | 37.76 | 2.52 | 5.04 | 2.52 |
| Example 20 | 0.69 | 0.69 | | 13.76 | 13.76 | 55.03 | 11.01 | 2.75 | 1.38 |
| Example 21 | 0.77 | 0.77 | | 30.71 | 23.03 | 30.71 | 3.07 | 6.14 | 3.07 |
| Example 22 | 0.68 | 0.68 | | 40.59 | 6.77 | 40.59 | 5.41 | 1.35 | 0.68 |
| Example 23 | 0.81 | | 0.81 | 16.11 | 24.17 | 48.34 | 3.22 | 3.22 | 1.61 |
| Example 24 | 0.65 | | 0.65 | 25.84 | 6.46 | 51.68 | 5.17 | 5.17 | 2.58 |

TABLE 1-continued

| | | | | | | | | | |
|---|---|---|---|---|---|---|---|---|---|
| Comparative Example 30 | 0.70 | | 0.70 | 41.70 | 13.90 | 27.80 | 11.12 | 1.39 | 0.70 |
| Comparative Example 31 | 1.25 | | | 25.03 | 12.52 | 50.06 | 5.01 | 2.50 | 1.25 |
| Example 25 | 0.73 | | | 29.09 | 14.54 | 43.63 | 5.82 | 2.91 | 1.45 |
| Example 26 | 0.49 | | | 29.57 | 14.79 | 39.43 | 7.89 | 3.94 | 1.97 |
| Comparative Example 32 | 0.41 | 0.41 | | 16.45 | 8.23 | 49.35 | 13.16 | 6.58 | 3.29 |
| Comparative Example 33 | 0.33 | 0.33 | | 26.35 | 13.18 | 52.70 | 2.64 | 1.32 | 0.66 |

| | Component (c) | | | Component (d) | | | | |
|---|---|---|---|---|---|---|---|---|
| | Red 3013 | Yellow 5GF | Blue 5050A | JR-805 | T60-23 | T60-21 | Contrast ratio | C* |
| Comparative Example 27 | 0.16 | | | 0.79 | 0.79 | | 0.71 | 36.52 |
| Comparative Example 28 | 0.15 | | | 0.77 | 3.07 | | 0.67 | 35.83 |
| Comparative Example 29 | 0.15 | | | 0.75 | 5.96 | | 0.79 | 36.05 |
| Example 15 | | 0.04 | | | 0.40 | | 0.17 | 8.97 |
| Example 16 | | 0.04 | | | 0.79 | | 0.22 | 13.29 |
| Example 17 | | 0.04 | | | 1.57 | | 0.30 | 17.74 |
| Example 18 | | 0.04 | | | 3.10 | | 0.45 | 18.94 |
| Example 19 | | 0.16 | | | 0.40 | | 0.21 | 10.51 |
| Example 20 | | 0.16 | | | 0.79 | | 0.26 | 13.87 |
| Example 21 | | 0.16 | | | 1.57 | | 0.39 | 19.10 |
| Example 22 | | 0.15 | | | 3.10 | | 0.52 | 22.22 |
| Example 23 | | 0.04 | 0.10 | | 1.57 | | 0.45 | 12.63 |
| Example 24 | | 0.04 | 0.20 | | 1.57 | | 0.57 | 11.32 |
| Comparative Example 30 | | 0.04 | 0.39 | | 1.57 | | 0.67 | 10.50 |
| Comparative Example 31 | | 0.04 | 0.78 | | 1.56 | | 0.79 | 10.88 |
| Example 25 | | 0.16 | 0.10 | | 1.57 | | 0.57 | 19.30 |
| Example 26 | | 0.16 | 0.20 | | 1.57 | | 0.37 | 19.26 |
| Comparative Example 32 | | 0.16 | 0.39 | | 1.57 | | 0.93 | 21.90 |
| Comparative Example 33 | | 0.16 | 0.78 | | 1.56 | | 0.90 | 21.51 |

What is claimed is:

1. An artificial nail composition consisting of:
a component (a): dimethacryloxyethyl-2,2,4-trimethyl-hexamethylene diurethane (UDMA), bisphenol A-diglycidyl methacrylate (BisGMA), tetradecaethylene glycol dimethacrylate (14G), bis[2-(methacryloxy)ethyl] phosphate (BisMEP), and 4-acryloxyethyltrimellitic acid (4AET),
a component (b): a member selected from the group consisting of 2,4,6-trimethylbenzoyl-diphenyl-phosphine oxide (MAPO), 2-hydroxy-2-methyl-1-phenyl-propan-1-one (DAR1173), 1-hydroxy-cyclohexyl-phenyl-ketone (IRG184) and a combination thereof;
a component (c): an organic colorant and titanium oxide, and
a component (d): an inorganic colorant having at least one kind of interference color, wherein the amount of the component (b) is 0.01 to 10 parts by weight, the amount of the organic colorant is 0.01 to 0.2 parts by weight, the amount of the titanium oxide is up to 0.3 parts by weight and the amount of the component (d) is 0.40 to 3.10 parts by weight with respect to 100 parts by weight of the component (a), and wherein a contrast ratio of the cured artificial nail composition is less than 0.6 when measured in accordance with JIS Z8701.

2. An artificial nail composition consisting of:
a component (a): dimethacryloxyethyl-2,2,4-trimethyl-hexamethylene diurethane (UDMA), bisphenol A-diglycidyl methacrylate (BisGMA), tetradecaethylene glycol dimethacrylate (14G), bis[2-(methacryloxy)ethyl] phosphate (BisMEP), and 4-acryloxyethyltrimellitic acid (4AET),
a component (b): a member selected from the group consisting of 2,4,6-trimethylbenzoyl-diphenyl-phosphine oxide (MAPO), 2-hydroxy-2-methyl-1-phenyl-propan-1-one (DAR1173), 1-hydroxy-cyclohexyl-phenyl-ketone (IRG184) and a combination thereof;
a component (c): an organic colorant, and
a component (d): an inorganic colorant having at least one kind of interference color, wherein the amount of the component (b) is 0.01 to 10 parts by weight, the amount of the organic colorant is 0.01 to 0.2 parts by weight, and the amount of the component (d) is 0.40 to 3.10 parts by weight with respect to 100 parts by weight of the component (a), and wherein a contrast ratio of the cured artificial nail composition is less than 0.6 when measured in accordance with JIS Z8701.

* * * * *